(12) United States Patent
Cossi et al.

(10) Patent No.: US 8,794,232 B2
(45) Date of Patent: Aug. 5, 2014

(54) DISPOSABLE MONODOSE INHALER FOR POWDERED MEDICAMENTS

(75) Inventors: Giampiero Cossi, Rome (IT); Mario La Barbera, Santa Flavia (IT); Marco Cecchini, Perugia (IT)

(73) Assignee: Giampiero Cossi, Magione PG (IT)

(*) Notice: Subject to any disclaimer, the term of this patent is extended or adjusted under 35 U.S.C. 154(b) by 1687 days.

(21) Appl. No.: 11/574,868

(22) PCT Filed: Sep. 16, 2004

(86) PCT No.: PCT/IT2004/000501
§ 371 (c)(1),
(2), (4) Date: Mar. 27, 2007

(87) PCT Pub. No.: WO2006/030459
PCT Pub. Date: Mar. 23, 2006

(65) Prior Publication Data
US 2007/0215151 A1      Sep. 20, 2007

(51) Int. Cl.
*A61M 15/00* (2006.01)
(52) U.S. Cl.
USPC ............ 128/203.15; 128/203.12; 128/203.23; 128/203.24
(58) Field of Classification Search
USPC ............. 128/203.12, 203.15, 203.21, 204.18, 128/200.23, 200.24
See application file for complete search history.

(56) References Cited

U.S. PATENT DOCUMENTS

| | | | | |
|---|---|---|---|---|
| 3,994,421 A * | 11/1976 | Hansen | ......................... | 222/182 |
| 4,648,393 A * | 3/1987 | Landis et al. | ............ | 128/200.23 |
| 4,846,168 A * | 7/1989 | Abiko et al. | ............. | 128/203.15 |
| 5,002,048 A * | 3/1991 | Makiej, Jr. | ............... | 128/200.23 |
| 5,113,855 A * | 5/1992 | Newhouse | ............... | 128/203.12 |
| 5,161,524 A * | 11/1992 | Evans | ...................... | 128/203.15 |
| 5,224,472 A * | 7/1993 | Pesenti et al. | ............ | 128/200.23 |
| 5,239,993 A * | 8/1993 | Evans | ...................... | 128/203.15 |
| 5,301,666 A | 4/1994 | Lerk et al. | | |
| 5,435,297 A | 7/1995 | Klein | | |
| 5,524,613 A * | 6/1996 | Haber et al. | ............. | 128/203.15 |
| 5,669,378 A | 9/1997 | Pera et al. | | |
| 5,823,183 A * | 10/1998 | Casper et al. | ............ | 128/203.15 |
| 6,089,227 A * | 7/2000 | Nilsson | .................... | 128/203.15 |
| 6,116,237 A * | 9/2000 | Schultz et al. | ........... | 128/203.15 |
| 6,397,840 B1 * | 6/2002 | Chrai et al. | .............. | 128/202.25 |
| 6,615,826 B1 * | 9/2003 | Gabrio et al. | ............ | 128/200.23 |
| 2003/0079743 A1 * | 5/2003 | Genova et al. | ........... | 128/203.12 |

* cited by examiner

*Primary Examiner* — Justine Yu
*Assistant Examiner* — Timothy Stanis
(74) *Attorney, Agent, or Firm* — Lucas & Mercanti, LLP

(57) ABSTRACT

A monodose inhaler for powdered medicaments consists of a hollow substantially pipe-shaped body that has a first portion (H), for housing a capsule or cartridge of powdered medicament, defined by a wall (W) in which there are formed slots (S) as air intakes to an inner region where the powder drops, and a second portion (M) connected to the first portion (H) for delivering the medicament by means of a primary stream (F) that carries the powder from the drop region along a delivery duct (D) whose end is suitable to be placed in the patient's mouth, and it further includes a secondary duct (D') located under the delivery duct (D) and provided with its own air intake (S') for delivering a powderless secondary stream (F').

14 Claims, 2 Drawing Sheets

Figure 5:
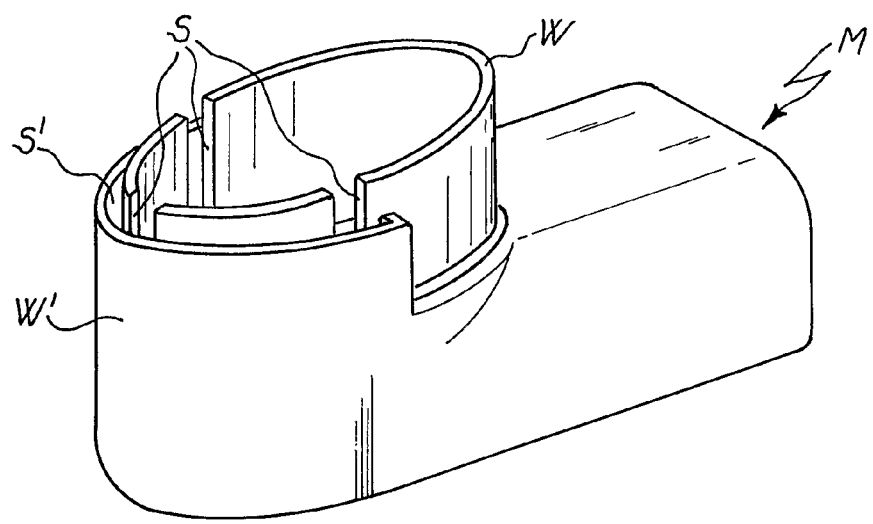
Figure 6:
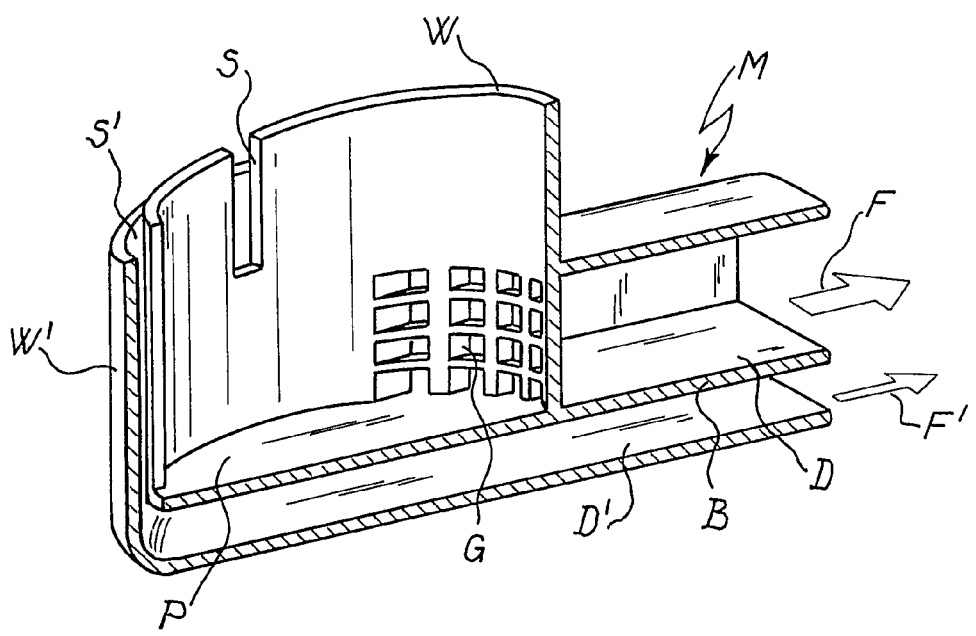

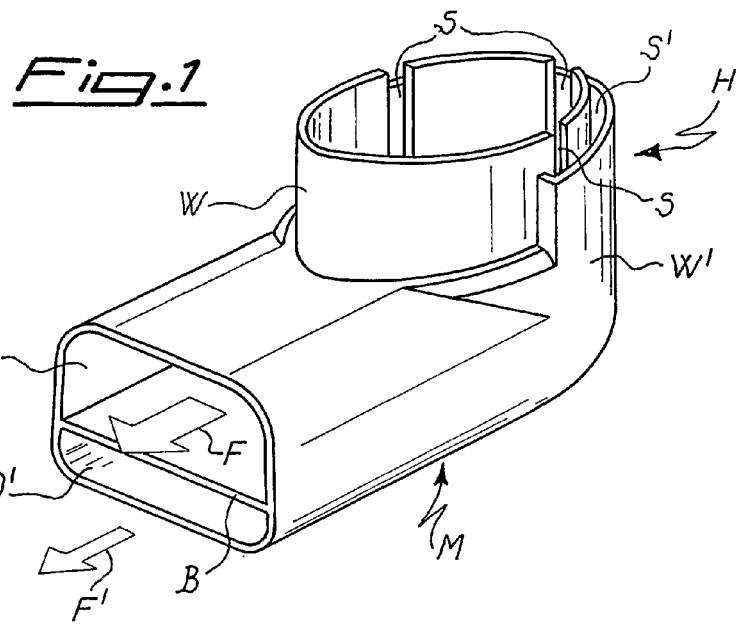
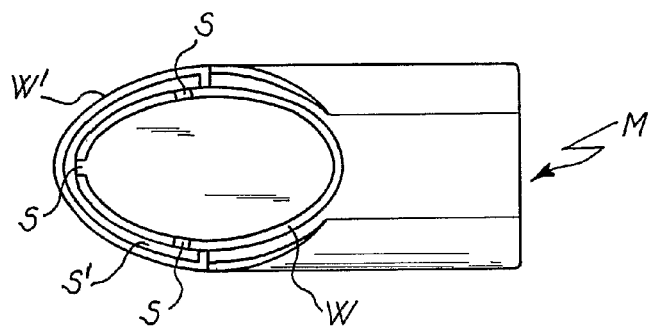
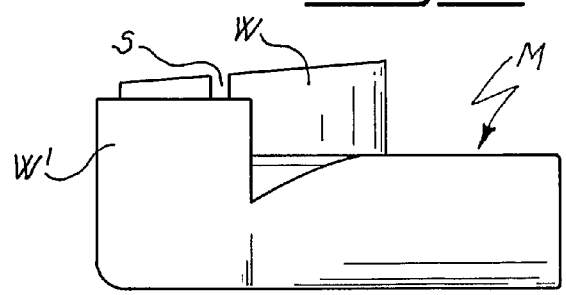
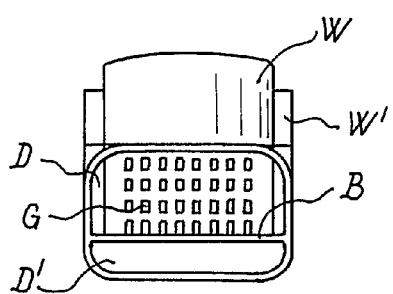

DISPOSABLE MONODOSE INHALER FOR POWDERED MEDICAMENTS

The present invention relates to inhalers for powdered medicaments, and in particular to a disposable monodose inhaler.

It is known that the administration of medicaments in the form of powders to be inhaled is an effective and non-invasive manner to provide a patient with the drug he requires. To this purpose, several devices, generally in the form of reusable multidose inhalers, have been designed to administer powdered medicaments.

This type of inhaler, however, has various drawbacks: a rather high cost; a significant complexity that makes its use rather difficult, in particular for elderly patients; a great difficulty in maintaining it in a satisfactory hygienic state over time; the risk that the powdered medicament is not properly delivered due to thickening or formation of a film caused by humidity or by other factors; the fact that usually most of the medicament does not reach the patient's lungs because it is deposited on the walls of mouth and throat.

In an attempt to overcome these drawbacks there was developed a monodose inhaler, disclosed in U.S. Pat. No. 5,669,378, that has a much simpler and cheaper structure and can therefore be used as a disposable inhaler. In this way there are no risks of poor hygiene and deterioration of the medicament, neither a significant difficulty in use.

In fact this type of inhaler essentially consists of a pipe-shaped body with a first portion, for housing a medicament-containing capsule, connected through a screen to a second portion, for delivering the powder, that the patient puts in his mouth. In order to release the powder from the capsule there is provided a button with a spike suitable to pierce the capsule placed in an adequate supporting member, a button-supporting spring being arranged between the button and the capsule-supporting member to prevent a premature piercing of the capsule.

Although this disposable monodose inhaler is a significant improvement with respect to previous multidose inhalers, yet it is also not free from drawbacks.

First of all, it does not solve the problem of the medicament being deposited in the oropharingeal cavity before reaching the lungs. As a consequence, if the patient does not receive the desired relief that he expects from the medicament, he tends to administer himself another dose prematurely with the risk of various unpleasant side effects caused by the overdose. Moreover, the medicament deposited in the oropharingeal cavity can cause some problems such as soreness, coughing, dryness and the like.

Secondly, it still requires assembling the above-mentioned three members (button, spring, capsule support) in the housing portion, which implies a certain manufacturing cost as well as the risk of a malfunction in case of defective assembly.

Therefore the object of the present invention is to provide a disposable monodose inhaler which is free from said drawbacks. This object is achieved by means of a monolithic inhaler provided with a bottom duct in the delivering portion and suitable to house an autoperforating cartridge.

The main advantage of the present inhaler is given by the presence of the secondary stream, delivered from the bottom duct, that supports and directs the primary stream, which carries the powdered medicament, so that the primary stream can climb over the patient's tongue. In this way there is prevented the excessive deposition of the medicament in the oropharingeal cavity and there is obtained a greater effectiveness of the treatment thanks to the larger amount of medicament that reaches the lungs.

A further advantage provided by the presence of the secondary stream is the better separation of the drug from the excipient (usually lactose) due to the secondary stream that hits and directs the primary stream.

Still another advantage of this inhaler is its low cost, thanks to the fact that notwithstanding the presence of the bottom duct it can still be manufactured in plastic by injection molding with a monolithic structure. Moreover, this inhaler is suitable to house an autoperforating cartridge, like the cartridge disclosed in WO 03/011708 in the name of one of the inventors, whereby the other members for capsule piercing described in the above-mentioned prior art inhaler can be dispensed with.

Further advantages and characteristics of the inhaler according to the present invention will be clear to those skilled in the art from the following detailed description of an embodiment thereof, with reference to the annexed drawings wherein:

1*a* FIG. 1 is a front perspective view of the inhaler;

1*a* FIG. 2 is a top plan view of the inhaler;

1*a* FIG. 3 is a side view of the inhaler;

1*a* FIG. 4 is a front view of the inhaler;

1*a* FIG. 5 is a rear perspective view of the inhaler; and

1*a* FIG. 6 is a sectional rear perspective view taken along the longitudinal midplane of the inhaler.

With reference to said figures, there is seen that an inhaler according to the present invention conventionally consists of a hollow substantially pipe-shaped body that has a first portion H, for housing the capsule or cartridge of the powdered medicament, and a second portion M, for delivering the medicament through a delivery duct D whose end is suitable to be placed in the patient's mouth.

In the wall W that defines the housing portion H there are formed one or more vertical slots S to provide air intakes to the inner region P where the powder drops. In the illustrated embodiment there are provided three slots S, namely a central slot extending through the whole height of wall W at the midplane in distal position and other two shorter slots symmetrically arranged with respect to the central slot.

The connection between the powder drop region P and the delivery duct D is achieved through a grid G sized to prevent the passage of pieces of the capsule or cartridge that should drop therefrom upon release of the powder.

The air entering through slots S forms a stream F that carries the powder from region P, through grid G, along the delivery duct D up to the patient's mouth.

The main novel aspect of the present inhaler is that it is designed to generate also a secondary, powderless, stream F' that supports and directs the primary stream F upon inhalation.

To this purpose, in the housing portion H there is provided a second wall W' that encloses wall W at least partially, for example along the rear half of the latter in the illustrated embodiment, and is spaced therefrom so as to obtain an interspace S' between the two walls.

This interspace S' continues below the powder drop region P and extends up to the end of the delivery duct D thus forming a bottom duct D'. In practice, the delivering portion M results therefore consisting of two ducts D, D' one on top of the other separated by a horizontal baffle B.

It is therefore clear that when the patient draws in air to inhale the powder located in region P, where it was released preferably from an autoperforating cartridge as mentioned above, a portion of the air passes through slots S and forms the primary powder-carrying stream F delivered through duct D, while another portion of the air passes through interspace S' and forms the secondary powderless stream F' delivered through the secondary duct D'.

As previously mentioned, the secondary stream F' supports the primary stream F and prevents the powder from depositing, also due to gravity, on the patient's tongue or on other walls of the oropharingeal cavity. This supporting and directing function is particularly important in case the patient holds the distal end of the inhaler too much inclined upwards.

This supporting effect, as well as the other effect of separation of the drug from the excipient, can be increased or decreased by changing the ratio between the cross-sections of ducts D, D' and/or between the cross-sections of the air intakes S, S' or other details. In other words, the two streams F, F' can be adjusted through the design of the various parts of the inhaler in order to obtain several embodiments with different inhalation characteristics for different specific applications.

For example, the air intake S' for the secondary stream F' could be formed directly at the rear end of the secondary duct D', in which case wall W' would extend only below the powder drop region P. Also, the dividing baffle B could be U-shaped rather than plane, so that the "air cushion" formed by the secondary stream F' partially encloses the primary stream F also on the sides.

It is clear that the above-described and illustrated embodiment of the inhaler according to the invention is just an example susceptible of various modifications. In particular, although portions H, M have been illustrated as connected at 90° it is clear that the monolithic body of the inhaler can be made also with any other angle between said portions from 0° to 90°, e.g. 45° or 60°. Moreover, the number, shape and arrangement of the air intakes to the powder drop region P can be freely changed and therefore be completely different from the above-illustrated slots S.

The invention claimed is:

1. An inhaler for powdered medicaments, comprising:
a hollow substantially pipe-shaped body having a first portion for housing a capsule or cartridge of powdered medicament, defined by a first wall in which there are formed one or more primary air intakes to an inner, powder drop region where the powdered medicament drops; and
a second portion connected to said first portion for delivering the powdered medicament by means of a primary stream from said powder drop region along a delivery duct having an end forming a first part of a mouthpiece with a predetermined length, said mouthpiece being suitable for placement in a patient's mouth, said delivery duct being part of said second portion, wherein, under said delivery duct, is a secondary duct having a secondary air intake for delivering a powderless secondary stream, said secondary duct being part of said second portion and being separated from said delivery duct by means of a dividing baffle, said secondary duct having an end forming a second part of said mouthpiece with said dividing baffle which is disposed between said delivery duct and said secondary duct, said dividing baffle extending the predetermined length of the mouthpiece whereby excessive deposition of the powdered medicament to the patent's oropharingeal cavity is inhibited, and
wherein said inhaler is manufactured from plastic by injection molding with a monolithic structure.

2. The inhaler according to claim 1, wherein the first portion has a second wall that encloses at least partially the first wall and is spaced therefrom so as to obtain an interspace that extends below the powder drop region and acts as the secondary air intake for the secondary duct.

3. The inhaler according to claim 2, wherein the primary air intakes to the powder drop region are three through slots.

4. The inhaler according to claim 2, wherein a grid is arranged between the powder drop region and the delivery duct.

5. The inhaler according to claim 2, wherein the first portion and the second portion of the body are connected at 90°.

6. The inhaler according to claim 1 wherein the primary air intakes to the powder drop region are three through slots.

7. The inhaler according to claim 6, wherein the three through slots are a central slot extending the entire height of the wall at a midplane in a distal position and other two slots, which are shorter than the central slot, are symmetrically arranged with respect to the central slot.

8. The inhaler according to claim 7, wherein a grid is arranged between the powder drop region and the delivery duct.

9. The inhaler according to claim 7, wherein the first portion and the second portion of the body are connected at 90°.

10. The inhaler according to claim 6, wherein a grid is arranged between the powder drop region and the delivery duct.

11. The inhaler according to claim 6, wherein the first portion and the second portion of the body are connected at 90°.

12. The inhaler according to claim 1, wherein a grid is arranged between the powder drop region and the delivery duct.

13. The inhaler according to claim 12, wherein the first portion and the second portion of the body are connected at 90°.

14. The inhaler according to claim 1, wherein the first portion and the second portion of the body are connected at 90°.

* * * * *

UNITED STATES PATENT AND TRADEMARK OFFICE
CERTIFICATE OF CORRECTION

Page 1 of 2

PATENT NO. : 8,794,232 B2
APPLICATION NO. : 11/574868
DATED : August 5, 2014
INVENTOR(S) : Giampiero Cossi et al.

It is certified that error appears in the above-identified patent and that said Letters Patent is hereby corrected as shown below:

IN THE CLAIMS:

Column 4, line 17 in claim 3,
"claim 2" should read --"claim 1"--.

Column 4, line 19 in claim 4,
"claim 2" should read --"claim 1"--.

Column 4, line 22 in claim 5,
"claim 2" should read --"claim 1"--.

Column 4, line 24 in claim 6,
"claim 1" should read --"claim 2"--.

Column 4, line 26 in claim 7,
"claim 6" should read --"claim 3"--.

Column 4, line 31 in claim 8,
"claim 7" should read --"claim 2"--.

Column 4, line 34 in claim 9,
"claim 7" should read --"claim 3"--.

Column 4, line 39 in claim 11,
"claim 6" should read --"claim 2"--.

Column 4, line 42 in claim 12,
"claim 1" should read --"claim 3"--.

Signed and Sealed this
Twenty-fifth Day of November, 2014

Michelle K. Lee
*Deputy Director of the United States Patent and Trademark Office*

CERTIFICATE OF CORRECTION (continued)
U.S. Pat. No. 8,794,232 B2

Column 4, line 45 in claim 13,
"claim 12" should read --"claim 4"--.

Column 4, line 48 in claim 14,
"claim 1" should read --"claim 7"--.